(12) United States Patent
Lee et al.

(10) Patent No.: US 12,121,701 B2
(45) Date of Patent: Oct. 22, 2024

(54) SYSTEMS AND METHODS FOR INCORPORATING CO-FORMULATIONS OF INSULIN IN AN AUTOMATIC INSULIN DELIVERY SYSTEM

(71) Applicant: Insulet Corporation, Acton, MA (US)

(72) Inventors: Joon Bok Lee, Acton, MA (US); Jason O'Connor, Acton, MA (US); Yibin Zheng, Hartland, WI (US); Ashutosh Zade, San Diego, CA (US)

(73) Assignee: INSULET CORPORATION, Acton, MA (US)

( * ) Notice: Subject to any disclaimer, the term of this patent is extended or adjusted under 35 U.S.C. 154(b) by 452 days.

(21) Appl. No.: 17/582,349

(22) Filed: Jan. 24, 2022

(65) Prior Publication Data
US 2022/0241504 A1     Aug. 4, 2022

Related U.S. Application Data

(60) Provisional application No. 63/143,437, filed on Jan. 29, 2021.

(51) Int. Cl.
*G16H 20/17*     (2018.01)
*A61B 5/00*      (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC .............................................. G06Q 50/20–26
See application file for complete search history.

(56) References Cited

U.S. PATENT DOCUMENTS

| 303,013 A | 8/1884 | Horton |
|---|---|---|
| 2,797,149 A | 6/1957 | Skeggs |

(Continued)

FOREIGN PATENT DOCUMENTS

| AU | 2015200834 A1 | 3/2015 |
|---|---|---|
| AU | 2015301146 A1 | 3/2017 |

(Continued)

OTHER PUBLICATIONS

US 5,954,699 A, 09/1999, Jost et al. (withdrawn)
(Continued)

*Primary Examiner* — Neal Sereboff
(74) *Attorney, Agent, or Firm* — GOODWIN PROCTER LLP

(57) ABSTRACT

Disclosed herein are systems and methods for the delivery of a co-formulation of insulin and a second drug, such as GLP-1, using an automated insulin delivery system. In a first embodiment, a dose of insulin is calculated by a medication delivery algorithm and a reduction factor is applied to account for the effect of second drug on the user's daily insulin requirement. In a second embodiment of the invention, a total amount of the second drug administered to the user during the past 24 hours is used to modify the correction factor and the insulin-to-carbohydrate ratio used by the medication delivery algorithm to cause a reduction in the insulin delivered to the user to account for the effect of the administration of the second drug portion of the co-formulation.

5 Claims, 3 Drawing Sheets

(51) Int. Cl.
*A61B 5/145* (2006.01)
*A61K 38/22* (2006.01)
*A61K 38/26* (2006.01)
*A61K 38/28* (2006.01)
*A61M 5/14* (2006.01)
*A61M 5/142* (2006.01)
*A61M 5/172* (2006.01)
*G16H 40/67* (2018.01)

(52) U.S. Cl.
CPC .......... *A61B 5/4866* (2013.01); *A61B 5/7282* (2013.01); *A61K 38/22* (2013.01); *A61K 38/26* (2013.01); *A61K 38/28* (2013.01); *A61M 5/1408* (2013.01); *A61M 5/14248* (2013.01); *G16H 20/17* (2018.01); *G16H 40/67* (2018.01); *A61M 2205/502* (2013.01); *A61M 2205/52* (2013.01); *A61M 2205/8206* (2013.01); *A61M 2230/201* (2013.01)

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |

(56) References Cited

U.S. PATENT DOCUMENTS

| | | |
|---|---|---|
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |

(56) References Cited

U.S. PATENT DOCUMENTS

| | | |
|---|---|---|
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | L. Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |

(56) References Cited

U.S. PATENT DOCUMENTS

| | | |
|---|---|---|
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0021978 A1* | 1/2012 | Werner .............. A61K 38/28 514/6.3 |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0200426 A1 | 1/2014 | Taub et al. |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0199452 A1* | 7/2016 | Souhami .............. A61P 3/10 514/6.5 |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |

(56) References Cited

U.S. PATENT DOCUMENTS

| | | | |
|---|---|---|---|
| 2022/0023536 A1 | 1/2022 | Graham et al. | |
| 2022/0062621 A1* | 3/2022 | Hogg | G09B 19/0092 |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 2139382 A1 | 1/2010 |
| EP | 2397181 A1 | 12/2011 |
| EP | 2666520 A1 | 11/2013 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 1571582 B1 | 4/2019 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 200032258 A1 | 6/2000 |
| WO | 0172354 A2 | 10/2001 |
| WO | 2002015954 A1 | 2/2002 |
| WO | 2002043866 A2 | 6/2002 |
| WO | 2002082990 A1 | 10/2002 |
| WO | 2003016882 A1 | 2/2003 |
| WO | 2003039362 A1 | 5/2003 |
| WO | 2003045233 A1 | 6/2003 |
| WO | 2004043250 A1 | 5/2004 |
| WO | 2005110601 A1 | 5/2004 |
| WO | 2004092715 A1 | 10/2004 |
| WO | 2005051170 A2 | 6/2005 |
| WO | 2005082436 A1 | 9/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

Differentiation of non-insulin producing cells into insulin producing cells by GLP-1 or Exendin-4 and uses thereof (Year: 1999).*

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Aogrithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, mailed May 16, 2017, 12 pages.

International Search Report and Written Opinion for the International Patent Application No. PCT/US2018/018901, mailed on Aug. 6, 2018, 12 pages.

(56) References Cited

OTHER PUBLICATIONS

International Search Report and Written Opinion for Application No. PCT/US2019/030562, Sep. 25, 2019, 19 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on IOS 11", GoToTags, Sep. 11, 2017, web <https://gototags.com/blog/read-nfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A "Microbial Contamination Of Haemodialysis Catheter Connections" Journal of Renal Care, European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al, "Multilumen Central Venous Catheters Increase Risk for Catheter-Related Bloodstream Infection: Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010 (OPTIS. 247VPC).
International Search Report and Written Opinion in PCT/US2008/079641 (Optis.203VPC) dated Feb. 25, 2009.
Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP—Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,vol. Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.

(56) References Cited

OTHER PUBLICATIONS

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Patent Office, "Notification of Transmittal of the ISR and the Written Opinion of the International Searching Authority, or the Declaration," in PCT Application No. PCT/GB2015/050248, Jun. 23, 2015, 12 pages.

International Search Report and Written Opinion for the International Patent Application No. PCT/US2021/012246, mailed Apr. 13, 2021, 15 pages.

International Search Report and Written Opinion for the International Patent Application No. PCT/US2021/013639, mailed Apr. 28, 2021, 14 pages.

International Search Report and Written Opinion for the International Patent Application No. PCT/US2020/063326, mailed May 3, 2021, 17 pages.

European Search Report for the European Patent Application No. 21168591, mailed Oct. 13, 2021, 4 pages.

International Search Report and Written Opinion for the International Patent Application No. PCT/US2021/041954, mailed Oct. 25, 2021, 13 pages.

International Search Report and Written Opinion for the International Patent Application No. PCT/US2021/022694, mailed Jun. 25, 2021, 13 pages.

International Search Report and Written Opinion for the International Patent Application No. PCT/US2021/017664, mailed May 26, 2021, 16 pages.

International Search Report and Written Opinion for the International Patent Application No. PCT/US2022/012896, mailed Apr. 22, 2022, 15 pages.

International Search Report and Written Opinion for the International Patent Application No. PCT/US2022/013470, mailed May 6, 2022, 14 pages.

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

International Search Report and Written Opinion for the International Patent Application No. PCT/US22/018700, mailed Jun. 7, 2022, 13 pages.

International Search Report and Written Opinion for the International Patent Application No. PCT/US22/019080, mailed Jun. 7, 2022, 14 pages.

International Search Report and Written Opinion for the International Patent Application No. PCT/US22/019664, mailed Jun. 7, 2022, 14 pages.

International Search Report and Written Opinion for International Patent Application No. PCT/US2021/051027, mailed on Jan. 7, 2022, 16 pages.

International Search Report and Written Opinion for International Patent Application No. PCT/US2021/052372, mailed Jan. 26, 2022, 15 pages.

International Search Report and Written Opinion for the International Patent Application No. PCT/US2021/046607, mailed Jan. 31, 2022, 20 pages.

International Search Report and Written Opinion for the International Patent Application No. PCT/US2021/055745, mailed Feb. 14, 2022, 13 pages.

International Search Report and Written Opinion for the International Patent Application No. PCT/US21/060618, mailed Mar. 21, 2022, 15 pages.

Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4,

(56) References Cited

OTHER PUBLICATIONS

XP055900328, Retrieved from the Internet: URL:https://github.com/MilosKozak/AndroidAPS/issues/2473 [retrieved on Jun. 6, 2022].

International Search Report and Written Opinion for the International Patent Application No. PCT/US2021/052855, mailed Dec. 22, 2021, 11 pages.

International Search Report and Written Opinion for the International Patent Application No. PCT/US2021/047771, mailed Dec. 22, 2021, 11 pages.

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

\* cited by examiner

SYSTEMS AND METHODS FOR INCORPORATING CO-FORMULATIONS OF INSULIN IN AN AUTOMATIC INSULIN DELIVERY SYSTEM

RELATED APPLICATIONS

This application claims the benefit of U.S. Provisional Patent Application No. 63/143,437, filed Jan. 29, 2021, the contents of which are incorporated herein by reference in their entirety.

BACKGROUND

The use of Glucagon-like Peptide 1 receptor agonists (GLP-1s) for the treatment of Type 2 diabetes has grown significantly in the recent past. GLP-1s are known as an efficacious tool to reduce blood glucose levels and lower body weight, while providing cardiovascular benefits for people living with type 2 diabetes. The GLP-1 receptor agonists currently approved in the United States for the treatment of type 2 diabetes include exenatide (administered twice daily via a pen), liraglutide and lixisenatide (administered once daily via a pen), and once-weekly agents exenatide extended-release, albiglutide, semiglutide and dulaglutide, all delivered via a pen.

GLP-1s drive favorable efficacy via several unique mechanisms which have benefits for diabetes management. In particular, and most importantly, GLP-1s lower the glucose levels in the patient. In addition, they tend to suppress post-prandial glucagon release, delay stomach emptying, and increase insulin sensitivity. Additionally, GLP-1 receptor agonists can help with weight loss and result in less hypoglycemia when used in combination with insulin. As disclosed in this application, using a fixed-ratio treatment of GLP-1 and insulin via continuous subcutaneous infusion can increase patient use and further improve glycemic control.

GLP-1 has been known to have significant beneficial effects in endogenous insulin tolerance. Specifically, the combination treatment of GLP-1 receptor agonists with Insulin has shown significant improvements in both Type 1 and Type 2 diabetes users. In one study, users were given 0.6 mg, 1.2 mg, or 1.8 mg doses of GLP-1 agonist liraglutide for 12 weeks, and users with 1.2 or 1.8 mg doses showed significant insulin dose reductions. On average, a user with 1.2 mg dose per day reduced their insulin needs by 12.1U compared to their starting TDI of 71.2U, or −17%. When translated to estimated daily impact, a 1 mg daily dose would result in 14% reduction in the user's insulin needs.

Many conventional automatic drug delivery (AID) systems of automatic insulin delivery (AID) systems are well known, including, for example, drug delivery devices of the type shown in FIG. 1 as reference number 102. The drug delivery device 102 can be designed to deliver any type of liquid drug to a user. In specific embodiments, the drug delivery device can be, for example, an OmniPod® wearable drug delivery device manufactured by Insulet Corporation of Acton, Massachusetts. The drug delivery device can be a drug delivery device such as those described in U.S. Pat. Nos. 7,303,549, 7,137,964, or 6,740,059, each of which is incorporated herein by reference in its entirety.

AID systems are typically limited to delivering insulin to control the glucose concentration of people with type I diabetes. However, it may be feasible to incorporate other non-insulin drugs, such as GLP-1, for improved glucose control performance.

The use of co-formulated GLP-1 receptor agonists and insulin can allow significantly reduced overall insulin delivery for users, and thus a reduced risk of hypoglycemia and other side effects of insulin delivery (such as weight gain). However, the use of GLP-1 means users require less insulin to experience similar reductions in glucose concentrations. As such, AID drug delivery algorithms designed to control the delivery of insulin using an AID system will tend to over-deliver the insulin when GLP-1 has been administered to the user, whether manually or via the AID system. Therefore, it would be desirable to provide updated algorithms that take into account the effects of GLP-1 when a co-formulation of insulin and GLP-1 is being delivered by the AID system, to reduce the amount of insulin delivered to the user.

DEFINITIONS

As used herein, the term "liquid drug" should be interpreted to include any drug in liquid form capable of being administered by a drug delivery device via a subcutaneous cannula, including, for example, insulin, morphine, blood pressure medicines, chemotherapy drugs, fertility drugs, or the like, or co-formulations of two or more of GLP-1, pramlintide, and insulin.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Embodiments of the invention disclosed herein include various ways of delivering a co-formulation of insulin and GLP-1 using an AID system while taking into account the effects of the GLP-1 on the user's daily insulin requirements, thereby allowing an adjustment of the quantity of insulin delivered to the user by the AID system.

In a first embodiment of the invention, a method is disclosed that incorporates the effect of delivering a co-formulation of non-insulin drugs (e.g., GLP-1) and insulin to a user via an AID system to incorporate various changes in the amount of insulin required by virtue of the co-delivery of the GLP-1. In this embodiment, the algorithm calculates a quantity of insulin required to be delivered to the user, and also calculates a reduction factor based on the quantity of GLP-1 recently delivered to the user and applies the reduction factor to affect a reduction in the insulin delivered to the user.

In a second embodiment of the invention, a method is disclosed to incorporate changes in the user's clinical parameters representing insulin sensitivity (e.g., insulin-to-carbohydrate (I:C) ratio and correction factor) due to GLP-1 when delivering co-formulated GLP-1 and insulin formulations. The effect of the delivery of the GLP-1 can be used to modify the calculation of the user's correction factor and I:C ratio by converting the total amount of the co-formulated drug that was delivered during a most recent predetermined period of time (e.g., 24 hours) into the total amount of GLP-1 that has been delivered in a previous predetermined period of time (e.g., 24 hours). The modified I:C ratio and correction factor may then be used by the algorithm to modify the amount of insulin delivered to the user.

The I:C ratio is the primary clinical parameter utilized to convert the number of carbohydrates ingested by the users for each meal, into the amount of insulin bolus that should be delivered at time of ingestion to compensate for the resulting rise in blood glucose concentrations. The co-formulation of GLP-1 with insulin means that the user will require less insulin to compensate for this glucose rise due to carbohydrates due to increased insulin sensitivity, and thus the I:C ratio should be increased or adjusted accordingly. Similarly, the correction factor parameter is the primary clinical parameter utilized to convert a desired change in blood glucose concentrations into one or more required insulin doses. Specifically, the correction factor parameter presents the decrease in blood glucose concentration, in mg/dL, for each Unit of insulin delivered. The co-formulation of GLP-1 with insulin means less insulin is required to affect the same decrease in blood glucose concentration—therefore, the Correction Factor should also be increased or adjusted accordingly. As such, incorporation of the impact of the co-formulation of GLP-1 and insulin into adjustment of the I:C and the correction factor parameters present important opportunities for improvements in the quality of glucose control for insulin pump users.

While exemplary embodiments of the present disclosure refer to a co-formulation of insulin and GLP-1, other co-formulations or drug combinations may be used. For example, a co-formulation of insulin and pramlintide may be used; or a co-formulation of insulin and other types of glucagon-like peptides may be used.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

This disclosure presents various systems, components and methods for moving a liquid drug from a liquid reservoir in a drug delivery device, for example, a wearable drug delivery device to a patient interface, typically a needle or cannula. The embodiments described herein provide one or more advantages over conventional, prior art systems, components and methods, such as better blood glucose control, greater convenience, and less weight gain.

Various embodiments of the present invention include systems and methods for delivering a medication to a user using a wearable drug device (sometimes referred to herein as a "pod"), either autonomously, or in accordance with a wireless signal received from an electronic device. In various embodiments, the electronic device may be a user device comprising a smartphone, a smart watch, a smart necklace, a module attached to the drug delivery device, or any other type or sort of electronic device that may be worn or carried on the body of the user and that executes an algorithm that computes the times and dosages of delivery of the medication. For example, the user device may execute an algorithm that computes the times and dosages of delivery of insulin. The user device may also be in communication with a sensor, such as a glucose sensor, that collects data on a physical attribute or condition of the user, such as a glucose level. The sensor may be disposed in or on the body of the user and may be part of the wearable drug delivery device or may be a separate device. Alternatively, the wearable drug delivery device may be in communication with the sensor in lieu of or in addition to the communication between the sensor and the user device. The communication may be direct (if, e.g., the sensor is integrated with or otherwise a part of the wearable drug delivery device) or remote/wireless (if, e.g., the sensor is disposed in a different housing than the medical device). In these embodiments, the sensor and/or the wearable drug delivery device contain computing hardware (e.g., a processor, memory, firmware, etc.) that executes some or all of the algorithm that computes the times and dosages of delivery of the medication.

Figure 1:
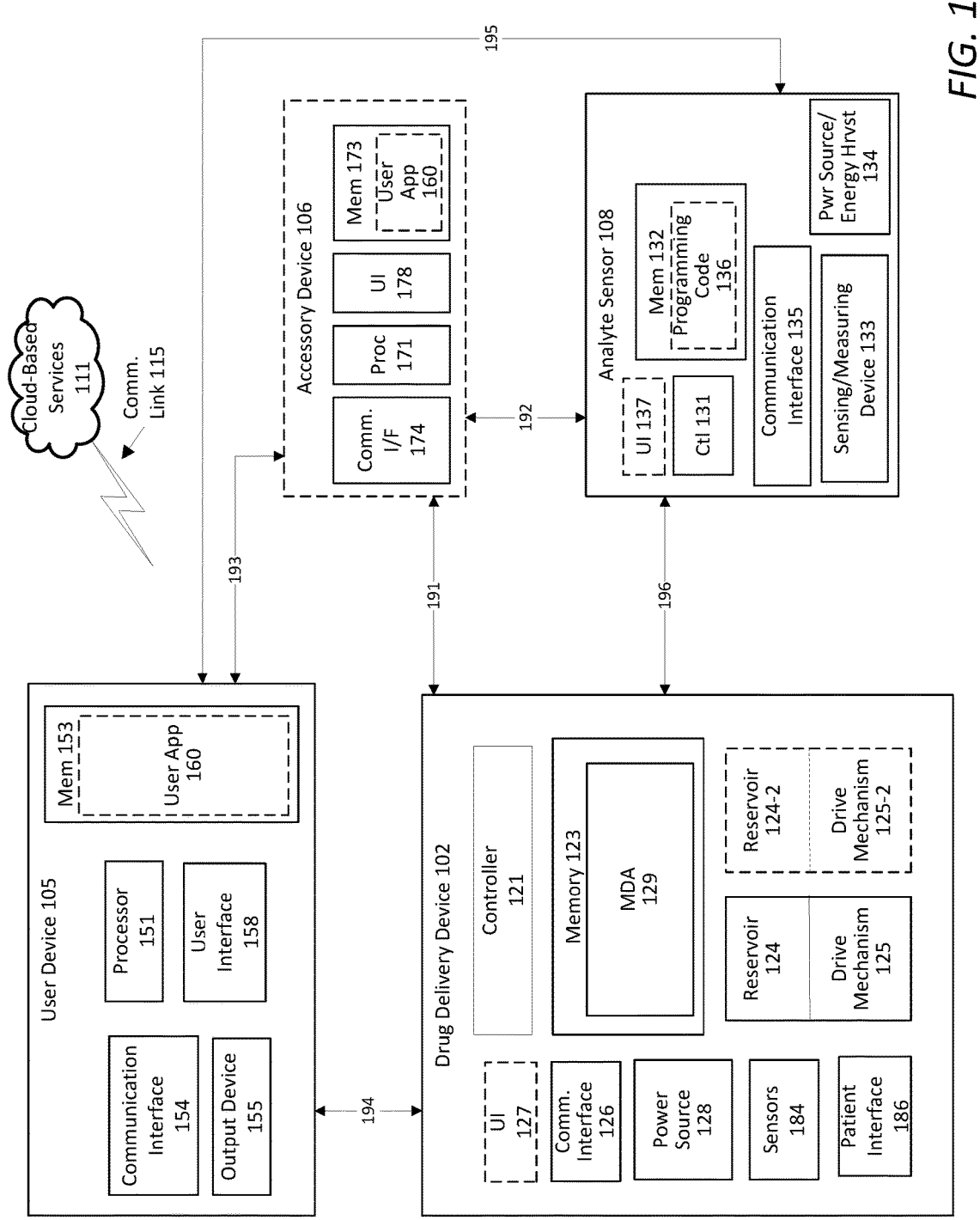
FIG. 1 illustrates a functional block diagram of an exemplary system suitable for implementing the systems and methods disclosed herein.

FIG. 1 illustrates a functional block diagram of an exemplary drug delivery system 100 suitable for implementing the systems and methods described herein. The drug delivery system 100 may implement (and/or provide functionality for) a medication delivery algorithm to govern or control automated delivery of a drug or medication, such as insulin, to a user (e.g., to maintain euglycemia—a normal level of glucose in the blood). The drug delivery system 100 may be an automated drug delivery system that may include a drug delivery device 102, an analyte sensor 108, and a user device 105.

The drug delivery system 100, in an optional example, may also include an accessory device 106, such as a smartwatch, a personal assistant device or the like, which may communicate with the other components of system 100 via either a wired or wireless communication links 191-193.

The user device 105 may be a computing device such as a smartphone, a tablet, a personal diabetes management (PDM) device, a dedicated diabetes therapy management device, or the like. In an example, user device 105 may include a processor 151, device memory 153, a user interface 158, and a communication interface 154. The user device 105 may also contain analog and/or digital circuitry that may be implemented as a processor 151 for executing processes based on programming code stored in device memory 153, such as user application 160 to manage a user's blood glucose levels and for controlling the delivery of the drug, medication, or therapeutic agent to the user, as well for providing other functions, such as calculating carbohydrate-compensation dosage, a correction bolus dosage and the like as discussed below. The user device 105 may be used to program, adjust settings, and/or control operation of the drug delivery device 102 and/or the analyte sensor 103 as well as the optional smart accessory device 106.

The processor 151 may also be configured to execute programming code stored in device memory 153, such as the user app 160. The user app 160 may be a computer application that is operable to deliver a drug based on information received from the analyte sensor 103, the cloud-based services 111 and/or the user device 105 or optional accessory device 106. The memory 153 may also store programming code to, for example, operate the user interface 158 (e.g., a touchscreen device, a camera or the like), the communication interface 154 and the like. The processor 151, when executing user app 160, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described herein.

In a specific example, when the user app 160 is an insulin delivery application, the processor 151 is also configured to execute a diabetes treatment plan (which may be stored in a memory) that is managed by user app 160. In addition to the functions mentioned above, when user app 160 is an insulin delivery application, it may further provide functionality to determine a carbohydrate-compensation dosage, a correction bolus dosage and determine a basal dosage according to a diabetes treatment plan. In addition, as an insulin delivery application, user app 160 provides functionality to output signals to drug delivery device 102 via communications interface 154 to deliver the determined bolus and basal dosages.

The communication interface 154 may include one or more transceivers that operate according to one or more radio-frequency protocols. In one embodiment, the transceivers may comprise a cellular transceiver and a Bluetooth® transceiver. The communication interface 154 may be configured to receive and transmit signals containing information usable by user app 160.

User device 105 may be further provided with one or more output devices 155 which may be, for example, a speaker or a vibration transducer, to provide various signals to the user.

An exemplary embodiment of the drug delivery device 102 may include a reservoir 124 and drive mechanism 125, which are controllable by controller 121, executing a medication delivery algorithm (MDA) 129 stored in memory 123. Alternatively, controller 121 may act to control reservoir 124 and drive mechanism 125 based on signals received from user app 160 executing on a user device 105 and communicated to drug delivery device 102 via communication link 194.

Drug delivery device 102 may further include a user interface 127, a patient interface 186, a communication interface 126, device sensors 184 and a power source 128.

In an alternate embodiment, drug delivery device 102 may also include an optional second reservoir 124-2 and second drive mechanism 125-2 which enables the independent delivery of two different liquid drugs, not as co-formulations in the same reservoir. As an example, reservoir 124 may be filled with insulin, while reservoir 124-2 may be filled with Pramlintide or GLP-1. In some embodiments, each of reservoirs 124, 124-2 may be configured with a separate drive mechanism 125, 125-2, respectively, which may be separately controllable by controller 121 under the direction of MDA 129. Both reservoirs 124, 124-2 may be connected to a common patient interface 186.

Drug delivery device 102 may be optionally configured with a user interface 127 providing a means for receiving input from the user and a means for outputting information to the user. User interface 127 may include, for example, light-emitting diodes, buttons on a housing of the drug delivery device 102, a sound transducer, a micro-display, a microphone, an accelerometer for detecting motions of the device of user gestures (e.g., tapping on a housing of the device) or any other type of interface device that is configured to allow a user to enter information and/or allow the drug delivery device 102 to output information for presentation to the user (e.g., alarm signals or the like).

The drug delivery device 102 includes a patient interface 186 for interfacing with the user to deliver the liquid drug. Patient interface may be, for example, a needle or cannula for delivering the drug into the body of the user (which may be done subcutaneously, intraperitoneally, or intravenously).

Drug delivery device 102 further includes a means for inserting the patient interface 186 into the body of the user which may comprise, in one embodiment, an actuator that inserts the needle/cannula under the skin of the user and thereafter retracts the needle, leaving the cannula in place.

In one embodiment, the drug delivery device 102 includes a communication interface 126, which may be a transceiver that operates according to one or more radio-frequency protocols, such as Bluetooth, Wi-Fi, near-field communication, cellular, or the like. The controller 121 may, for example, communicate with user device 105 and an analyte sensor 108 via the communication interface 126.

In some embodiments, drug delivery device 102 may be provided with one or more sensors 184. The sensors 184 may include one or more of a pressure sensor, a power sensor, or the like that are communicatively coupled to the controller 121 and provide various signals. For example, a pressure sensor may be configured to provide an indication of the fluid pressure detected in a fluid pathway between the patient interface 186 and reservoir 124. The pressure sensor may be coupled to or integral with the actuator for inserting the patient interface 186 into the user. In an example, the controller 121 may be operable to determine a rate of drug infusion based on the indication of the fluid pressure. The rate of drug infusion may be compared to an infusion rate threshold, and the comparison result may be usable in determining an amount of insulin onboard (IOB) or a total daily insulin (TDI) amount.

Drug delivery device 102 further includes a power source 128, such as a battery, a piezoelectric device, an energy harvesting device, or the like, for supplying electrical power to controller 121, memory 123, drive mechanisms 125 and/or other components of the drug delivery device 102.

The communication link 115 that couples the cloud-based services 111 to the respective devices 102, 105, 106, 108 of system 100 may be a cellular link, a Wi-Fi link, a Bluetooth link, or a combination thereof. Services provided by cloud-based services 111 may include data storage that stores anonymized data, such as blood glucose measurement values, historical IOB or TDI, prior carbohydrate-compensation dosage, and other forms of data. In addition, the cloud-based services 111 may process the anonymized data from multiple users to provide generalized information related to TDI, insulin sensitivity, IOB and the like.

The wireless communication links 191-196 may be any type of wireless link operating using known wireless communication standards or proprietary standards. As an example, the wireless communication links 191-196 may provide communication links based on Bluetooth®, Zigbee®, Wi-Fi, a near-field communication standard, a cellular standard, or any other wireless protocol via the respective communication interfaces 154, 174, 126 and 135.

The drug delivery device 102 may be configured to perform and execute processes required to deliver doses of the medication to the user without input from the user device 105 or the optional accessory device 106. As explained in more detail, MDA 129 may be operable, for example, to determine an amount of insulin to be delivered, JOB, insulin remaining, and the like and to cause controller 121 to control drive mechanism 125 to deliver the medication from reservoir 124. MDA 129 may take as input data received from the analyte sensor 108 or from user app 160.

The reservoirs 124, 124-2 may be configured to store drugs, medications or therapeutic agents suitable for automated delivery, such as insulin, Pramlintide, GLP-1, co-formulations of insulin and GLP-1, morphine, blood pressure medicines, chemotherapy drugs, fertility drugs, or the like.

The drug delivery device 102 may be attached to the body of a user, such as a patient or diabetic, at an attachment location and may deliver any therapeutic agent, including any drug or medicine, such as insulin, a co-formulation as described above, or the like, to a user at or around the attachment location. A surface of the drug delivery device 102 may include an adhesive to facilitate attachment to the skin of a user.

When configured to communicate with an external device, such as the user device 105 or the analyte sensor 108, the drug delivery device 102 may receive signals via link 194 from the user device 105 or via link 196 from the analyte sensor 108. The controller 121 of the drug delivery device 102 may receive and process the signals from the respective external devices as well as implementing delivery of a drug to the user according to a diabetes treatment plan or other drug delivery regimen, implemented by MDA 129 or user application 160.

In an operational example, the controller 121, when executing MDA 129 may generate and output a control signal operable to actuate the drive mechanism 125 to deliver a carbohydrate-compensation dosage of insulin, a correction bolus, a revised basal dosage, co-formulations of various liquid drugs, or the like.

The accessory device 106 may be, for example, an Apple Watch®, other wearable smart device, including eyeglasses, smart jewelry, a global positioning system-enabled wearable, a wearable fitness device, smart clothing, or the like. Similar to user device 105, the accessory device 106 may also be configured to perform various functions including controlling the drug delivery device 102. For example, the accessory device 106 may include a communication interface 174, a processor 171, a user interface 178 and a memory 173. The user interface 178 may be a graphical user interface presented on a touchscreen display of the smart accessory device 106. The memory 173 may store programming code to operate different functions of the smart accessory device 106 as well as an instance of the user app 160, or a pared-down versions of user app 160 with reduced functionality.

The analyte sensor 108 may include a controller 131, a memory 132, a sensing/measuring device 133, an optional user interface 137, a power source/energy harvesting circuitry 134, and a communication interface 135. The analyte sensor 108 may be a continuous glucose monitor (CGM) and may be communicatively coupled to the processor 151 of the management device 105 or controller 121 of the drug delivery device 102. The memory 132 may be configured to store information and programming code 136.

The analyte sensor 108 may be configured to detect one or multiple different analytes, such as glucose, lactate, ketones, uric acid, sodium, potassium, alcohol levels or the like, and output results of the detections, such as measurement values or the like. The analyte sensor 108 may, in an exemplary embodiment, be configured as a continuous glucose monitor (CGM) to measure blood glucose values at predetermined time intervals, such as every 5 minutes, or the like. The communication interface 135 of analyte sensor 108 may have circuitry that operates as a transceiver for communicating the measured blood glucose values to the user device 105 over a wireless link 195 or with drug delivery device 102 over the wireless communication link 108. While referred to herein as an analyte sensor 108, the sensing/measuring device 133 of the analyte sensor 108 may include one or more additional sensing elements, such as a glucose measurement element, a heart rate monitor, a pressure sensor, or the like. The controller 131 may include discrete, specialized logic and/or components, an application-specific integrated circuit, a microcontroller or processor that executes software instructions, firmware, programming instructions stored in memory (such as memory 132), or any combination thereof.

Similar to the controller 221 of drug delivery device 102, the controller 131 of the analyte sensor 108 may be operable to perform many functions. For example, the controller 131 may be configured by programming code 136 to manage the collection and analysis of data detected by the sensing and measuring device 133.

Although the analyte sensor 108 is depicted in FIG. 1 as separate from the drug delivery device 102, in various embodiments, the analyte sensor 108 and drug delivery device 102 may be incorporated into the same unit. That is, in various examples, the analyte sensor 108 may be a part of and integral with the drug delivery device 102 and contained within the same housing as the drug delivery device 102. In such an embodiment, the controller 221 may be able to implement the functions required for the proper delivery of the medication alone without any external inputs from user device 105, the cloud-based services 111, another sensor (not shown), the optional accessory device 106, or the like.

The user app 160 (or MDA 129) may provide periodic insulin micro-boluses based upon the predicted glucose over a 60-minute prediction horizon. The user app 160 or MDA 129 may compensate for missed meal boluses and mitigate prolonged hyperglycemia. The user app 160 or MDA 129 may use a control-to-target strategy that attempts to achieve and maintain a set target glucose value, thereby reducing the duration of prolonged hyperglycemia and hypoglycemia.

The user app 160 implements a graphical user interface that is the primary interface with the user and may be used to control, activate, or deactivate drug delivery device 102, program basal and bolus calculator settings for manual mode, as well as program settings specific for an automated mode (hybrid closed-loop or closed-loop).

In manual mode, user app 160 will deliver insulin at programmed basal rates and bolus amounts with the option to set temporary basal profiles. The controller 121 will also have the ability to function as a sensor-augmented pump in manual mode, using sensor glucose data provided by the analyte sensor 108 to populate the bolus calculator.

In automated mode, the user app 160 supports the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the user app 160 or MDA 129 for insulin dosing parameters. The insulin dosing parameters will be adapted over time based on the total daily insulin (TDI) delivered during each use of drug delivery device 102. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

User app 160, allows the use of large text, graphics, and on-screen instructions to prompt the user through the set-up processes and the use of system 100. It will also be used to program the user's custom basal insulin delivery profile, check the status, of drug delivery device 102, initiate bolus doses of insulin, make changes to a patient's insulin delivery profile, handle system alerts and alarms, and allow the user to switch between automated mode and manual mode.

In some embodiments, user device 105 and the analyte sensor 108 may not communicate directly with one another. Instead, data (e.g., blood glucose readings) from analyte sensor may be communicated to drug delivery device 102 via link 196 and then relayed to user device 105 via link 194. In some embodiments, to enable communication between analyte sensor 108 and user device 105, the serial number of the analyte sensor must be entered into user app 160.

User app 160 may provide the ability to calculate a suggested bolus dose through the use of a bolus calculator. The bolus calculator is provided as a convenience to the user to aid in determining the suggested bolus dose based on ingested carbohydrates, most-recent blood glucose readings (or a blood glucose reading if using fingerstick), programmable correction factor, insulin to carbohydrate ratio, target glucose value and insulin on board (IOB). IOB is estimated by user app 160 taking into account any manual bolus and insulin delivered by the algorithm.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In a first embodiment of the invention, drug delivery system 100 is configured with a drug delivery device 102 having single reservoir containing a co-formulation of GLP-1 and insulin. While exemplary embodiments of the present disclosure refer to a co-formulation of insulin and GLP-1, other co-formulations or drug combinations may be used. For example, a co-formulation of insulin and pramlintide may be used; or a co-formulation of insulin and other types of glucagon-like peptides may be used. In one example of the first embodiment, drug delivery device 102 stores enough insulin in reservoir 124 for three days (e.g., ~200 units), a three day supply of GLP-1 (e.g., ~3.5 mg) may be dissolved in the 200U of insulin. In this exemplary embodiment, the amount of GLP-1 that is delivered per pulse (i.e., per 0.05 units of insulin, which, in some embodiments, the smallest amount that can be delivered by drug delivery device 102) would be 0.0009 mg of GLP-1 per pulse. Specifically, in an exemplary embodiment, 200U of insulin provides 4000 actuations of 0.05U possible by one reservoir; if 3.5 mg of GLP-1 is dissolved in 200U of insulin, each actuation will deliver 3.5/4000, or ~0.0009 mg of GLP-1. This parameter may significantly vary depending on the reservoir of drug delivery, and the amount of maximum drug delivery per unit of action, for each insulin pump device. It is assumed that the quantity of GLP-1, when dissolved in the insulin, is small enough that the impact on the concentration of the insulin is negligible. In variations of the embodiment, different concentrations of GLP-1 may be used.

In this embodiment, a reduction factor is calculated based on the concentration of GLP-1 co-formulated with the insulin. Given the high volumetric difference between the amount of GLP-1 and insulin, the algorithm used by MDA 129 or user app 160 to calculate the doses of insulin may rely on the assumption that reservoir 124 contains only insulin. The calculated doses will then be reduced by the reduction factor to take into account the effect of the GLP-1 in reducing the user's need for insulin.

As previously stated, a 1 mg daily dose of GLP-1 will reduce the user's insulin needs by, on average, 14% (based on an average population of users). This can be used to calculate the reduction factor for the recommended insulin dose, based on the sum of all past insulin doses in the most recent predetermined time period (e.g., 24 hours), converted to the total GLP-1 delivered during the most recent predetermined time period (e.g., 24 hours), as follows:

$$R_{GLP1} = I_R \cdot \frac{\sum_{i=1}^{j} I(i)}{0.05} \cdot D_p \quad (1)$$

where:

$$\frac{\sum_{i=1}^{j} I(i)}{0.05}$$

is the total number of pulses of the co-formulation delivered during the past j is the number of cycles (e.g., j=288, assuming that the need for insulin is evaluated every 5 minutes during a most recent predetermined time period of 24 hours, as each new glucose reading is received;

$I_R$ is the reduction in the user's glucose requirement during the j number of cycles (e.g., 14% or 0.14); and $D_p$ is the amount of the drug constituent (e.g., GLP-1) that is actually being delivered per each 0.05U pulse (e.g., 0.0009 mg of GLP-1, which may vary depending on concentration of GLP-1 or other drug being dissolved, the total capacity of the reservoir, and the actuation unit of each pump device.

Eq. (1) can be generalized based on the concentration of GLP-1 as follows:

$$R_{GLP1} = I_R \cdot \frac{\sum_{i=1}^{j} I(i)}{0.05} \cdot \frac{GLP1_{total}}{x} \quad (2)$$

where:
$GLP1_{total}$ is the total amount of GLP-1 (in mg/dL) that is dissolved in the reservoir of the drug delivery device (e.g., 200U); and
x is the number of pulses in the quantity of the co-formulation in the reservoir (e.g., for a 200U quantity of the co-formulation, x=4000 when each pulse is 0.05U).

Once the reduction factor has been calculated, then any insulin delivery requests, whether based on manual or automated deliveries, can incorporate this insulin reduction factor as:

$$I_{final}(i) = (1 - R_{GLP1})I_{calc}(i) \quad (3)$$

where:

$I_{calc}(i)$ is the dose calculated by the algorithm for the $i^{th}$ cycle; and $I_{final}(i)$ is the reduced dose calculated after applying the reduction factor.

It should be noted that the reduction factor is reliant on the assumption that the user's daily insulin needs will be reduced by a factor of $I_R$ introduced above (e.g., 14%) by the introduction of the delivery of the GLP-1. As would be realized by one of skill in the art, the exemplary 14% may not apply equally to all users. Therefore, in variations of this embodiment, if the actual effect of the GLP-1 on a particular user is known, the reduction factor should be customized for that user by adjusting the factor $I_R$ introduced above. For example, a particular user may see a reduction in daily insulin need of greater or lesser than the average 14%. This individual percentage could be a programmable factor used by the algorithm of MDA 129 or user app 160.

Figure 2:
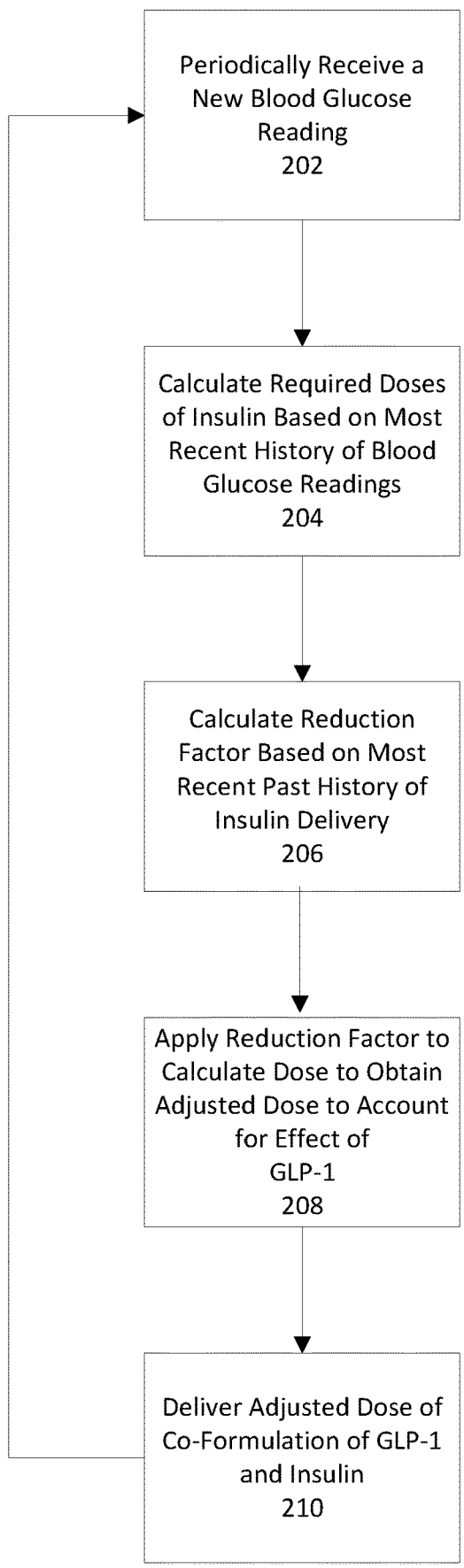
FIG. 2 is a flowchart showing a method of a first embodiment of the invention.

FIG. 2 is a flowchart showing flow of a method in accordance with the first embodiment of the invention. At 202, the drug delivery system 100 periodically receives a blood glucose reading of the user. For example, in certain embodiments, the drug delivery device 102 will receive blood glucose readings directly from the analyte sensor 108 via communication link 196. Based on the most recent history of received blood glucose readings, MDA 129 calculates, at 204, a required basal or bolus dose of insulin. Note that the algorithm of MDA 129 may calculate the required dose of insulin assuming that reservoir 124 contains only insulin.

At 206, MDA 129 calculates the reduction factor based on the history of doses delivered to the user during a past period of time (e.g., the past 24 hours), from which the total GLP-1 received by the user during the past period of time (e.g., 24 hours) can be calculated. In variations of this embodiment, other methods of calculating the reduction factor may be used. For example, the reduction factor may be based on a time period other than the most recent 24 hour period.

At 208, the reduction factor is applied to the calculated dose of insulin in accordance with Eq. (3) to obtain an adjusted dose. The calculated dose is reduced by the reduction factor to obtain the adjusted dose, which takes into account the user's reduced need for insulin based on the presence of the GLP-1 in the co-formulation. At 210, the adjusted dose of the co-formulation of GLP-1 and insulin is delivered to the user by drug delivery device 102.

The method shown in FIG. 2 has the advantage that the existing algorithm to calculate the required basal or bolus doses of insulin need not be modified but can be used to calculate the required doses of insulin as normal, assuming that no GLP-1 is being delivered. Thereafter, the reduction factor is calculated, and the calculated dose of insulin is reduced by the reduction factor to obtain the adjusted dose. The process is repeated for each cycle of the algorithm, that is, each time a new blood glucose reading is received.

In a second embodiment of the invention, drug delivery device 102 is also provided with a single reservoir 124 containing a co-formulation of GLP-1 and insulin. This embodiment discloses a method which incorporates changes in the user's clinical parameters representing insulin sensitivity (i.e., the insulin-to-carbohydrate (I:C) ratio, and the correction factor) due to GLP1 into the insulin delivery algorithms in drug delivery system 100 when delivering a co-formulation of GLP-1 and insulin.

Eq. (4) below converts the total amount of the co-formulation of GLP-1 and insulin that was delivered in a previous period of time (e.g., the previous 24 hours) into the total amount of GLP-1 that has been delivered in the previous period of time (e.g., 24 hours). Specifically, the units of the co-formulation can be converted into mL of the co-formulation that was delivered in the last 24 hours, then converted to the total amount of GLP-1 that has been delivered based on the concentration of the GLP-1 in the co-formulation. The total amount of GLP-1 that has been delivered in the previous period of time (e.g., the past 24 hours) is then incorporated into the calculation of the correction factor and the I:C ratio.

$$GLP_{Xh}(k) = C_{GLP} \cdot \frac{\sum_{i=1}^{j} I_{hist}(k-i)}{100} \quad (4)$$

where:

$C_{GLP}$ is the concentration of GLP (in mg/mL);

$$\frac{\sum_{i=1}^{j} I_{hist}(k-i)}{100}$$

is the amount of insulin that would have been delivered if GLP-1 was not taken into account;

j is the number of cycles in X hours (Xh, e.g., 24 h) (e.g., j=288, assuming that the need for insulin is evaluated every 5 minutes during a most recent predetermined time period of 24 hours, as each new glucose reading is received).

Eq. (4) also assumes that user is using U-100 insulin, (specifically, 100U is equal to 1 mL) and that the quantity of GLP-1 does not impact the concentration of insulin in the co-formulation.

In the case of incorporating these values in large boluses in a bolus calculator, the calculation of $GLP_{24\,h}$ should also take into account the user's expected changes in insulin sensitivity due to the additional GLP-1 that is delivered. This may be implemented by modifying the estimate of $GLP_{24\,h}$ as follows:

$$GLP_{24h,bolus}(k) = \quad (5)$$
$$C_{GLP} \cdot \frac{\left(\sum_{i=1}^{j} I_{hist}(k-i) + \left(\frac{CHO(k)}{IC(k)}\right) + \left(\frac{G(k) - SP(k)}{CF(k)} - IOB(k)\right)\right)}{100}$$

where:

j is the number of cycles (e.g., j=288 for a 24 hour period);

CHO(k) is the user's ingested grams of carbohydrates in the $k^{th}$ cycle;

IC(k) is the unmodified I:C ratio;

G(k) is the glucose reading for the $k^{th}$ cycle;

SP(k) is the target glucose or setpoint for the $k^{th}$ cycle;

CF(k) is the unmodified correction factor for the $k^{th}$ cycle; and

IOB(k) is the insulin on board for the $k^{th}$ cycle.

The divisor (100) in Eq. (5) represents a conversion between units (U) of insulin and mL of insulin.

The calculated $GLP_{24\,h}$ is then used to calculate a modified correction factor ($CF_{GLP}$) for the current ($k^{th}$) cycle as follows:

$$CF_{GLP}(k) = \frac{CF(k)}{(1 - I_R \cdot GLP_{24h}(k))} \quad (6)$$

The assumption that a 1 mg daily dose reduces the user's insulin requirement by an average of 14% may be used in Eq. (6) (i.e., $I_R$=14% or 0.014) to calculate a modified correction factor. The correction factor is used in the user's bolus calculations and can also be used by AID algorithms to calculate the user's IOB needs.

The I:C ratio, which is used in the calculation of the bolus doses of insulin, can also be updated in a similar manner:

$$IC_{GLP}(k) = \frac{IC(k)}{(1 - 0.14 \cdot GLP_{24h}(k))} \quad (7)$$

As with the first embodiment, the 14% reduction in daily insulin requirement may not apply equally to all users. Therefore, in variations of this embodiment, if the actual effect of the GLP-1 on a particular user is known, the reduction factor should be customized for that user and used as a programmable factor used by the algorithm of MDA 129 or user app 160.

The modification of the correction factor and the I:C ratio will cause the algorithm used by MDA 129 to calculate smaller bolus doses to be delivered to take in to account the effect of the GLP-1 on the user's daily insulin requirement.

Figure 3:
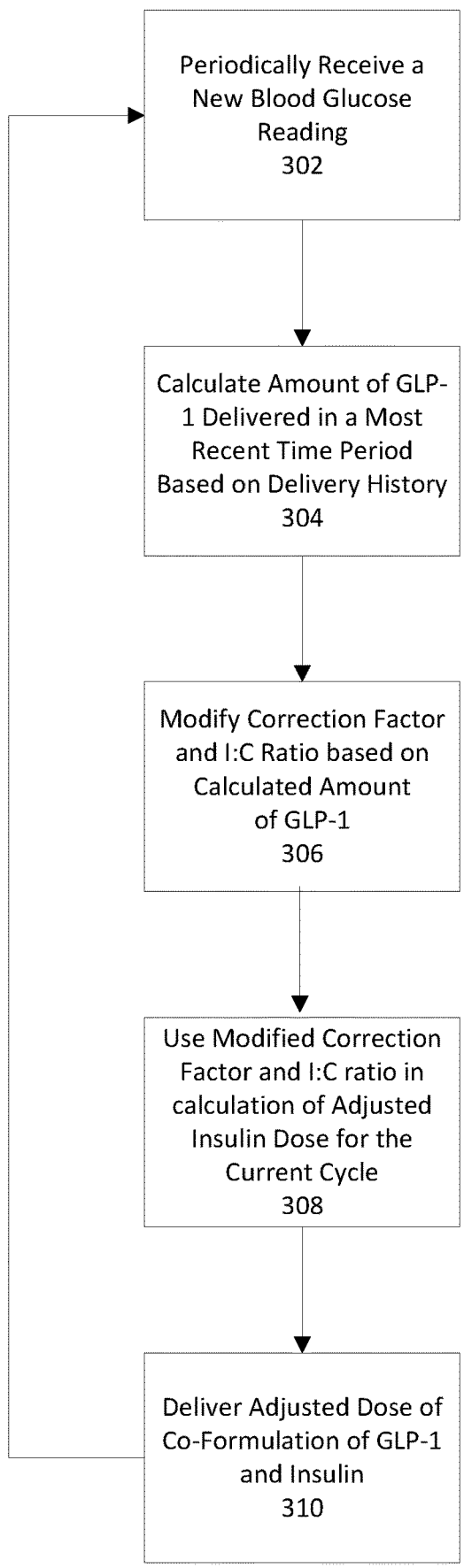
FIG. 3 is a flowchart showing a method of a second embodiment of the invention.

FIG. 3 is a flowchart showing flow of a method in accordance with the second embodiment of the invention. At 302, the drug delivery system 100 periodically receives a blood glucose reading of the user. For example, in certain embodiments, the drug delivery device 102 will receive blood glucose readings directly from the analyte sensor 108 via communication link 196.

Based on the most recent history of received blood glucose readings, MDA 129 calculates, at 304, the total amount of GLP-1 administered during a most recent time period, based on the history of delivered doses. In preferred embodiments of the invention, this time period is 24 hours, but other time periods may be used. This calculation may be different depending on whether a basal dose or a bolus dose of the co-formulation is being calculated, as explained above.

At 306, MDA 129 calculates a modified correction factor and I:C ratio, taking into account the GLP-1 delivered during the most recent time period, in accordance with Eqs. (6) and (7) respectively. At 308, the modified correction factor and I:C ratio are used to calculate an adjusted insulin dose and, at 310, the adjusted insulin dose is delivered to the user by drug delivery device 102.

The examples above refer to a set or pre-determined amount of a second drug, such as GLP-1, having been co-formulated with insulin. As users incorporate a co-formulation of insulin and GLP-1, pramlintide, or other drugs into their regimen, the co-formulation may initially be delivered with a fixed amount of each additional drug in the reservoir with insulin. As this provides a fixed amount of GLP-1 (or other drug) when delivered into the reservoir with insulin, or a fixed ratio of GLP-1 and insulin when co-formulated with a set amount of insulin, this amount or this ratio may not be ideal for all users, who may vary in their needs for GLP-1 that are independent from their insulin needs.

In a further exemplary embodiment, a method is disclosed for an insulin pump system to review the user's previously recorded daily insulin needs against their most recent insulin delivery history, and modify the concentration of GLP-1, pramlintide, or other drug, that is co-formulated with insulin for the next iteration of a pump reservoir refill. This can be done automatically via an auto reservoir fill mechanism, or done manually by the user based on a suggestion from the insulin pump system.

GLP1, pramlintide, and/or other co-formulated drugs with insulin may have fixed or personalized daily doses that may be recommended by a physician, which may be independent from the user's insulin needs. However, in co-formulated drugs, the amount of insulin the user receives per day may impact the amount of each co-formulated drug that the users may also receive.

In an exemplary embodiment, an automated or manual preparation of co-formulated drugs with insulin may initially apply a fixed amount of such drugs per one full reservoir, such as 200U of insulin (e.g., 3 mg of GLP1 per 200U).

This initial dose, $D_{co}$, can subsequently be adjusted based on the expected daily dose of each drug against the changes in the user's total insulin needs. Specifically, the final amount of each co-formulated drug that can be incorporated into the user's new reservoir fill can be adjusted as follows:

$$D_{co}(j) = D_{co}(1) \cdot \frac{TDI(1)}{TDI(j)}$$

where:
TDI(1) is the Total Daily Insulin (TDI) of the user during which the co-formulated drug was prescribed by the physician; and
TDI(j) is the user's adapted TDI for the next cycle when the user's TDI is reassessed, which may be based on the following exemplary weighting equation:

$$TDI(j) = (1 - 0.2 \cdot N_{days})TDI(j-1) + 0.2 \cdot N_{days} \sum I(j-1)$$

Note that this exemplary embodiment may reduce the suggested amount of co-formulated drug to be included with the new insulin reservoir. This is the case if, to maintain the same amount of total co-formulated drug dose to the user each day, as the user's daily insulin needs increase, the amount of drug being delivered per insulin dose must be decreased—which is achieved by reducing the overall amount of co-formulated drug that is being incorporated into the insulin reservoir. This results in a reduction in the concentration of the co-formulated drug within the insulin reservoir, and thus a reduction in the amount of the co-formulated drug being delivered per insulin dose. In cases where the user's adapted TDI for a next cycle (e.g., a three-day cycle of wearing an insulin pump) decreases, then $D_{co}(j)$, or the amount of the co-formulated drug for the next cycle or the new reservoir, may increase. To receive the same amount of secondary drug (e.g., GLP-1 or pramlintide) as the user receives less insulin, the concentration of the secondary drug in the insulin must be increased. In this manner, the ratio of the secondary drug and insulin may be adjusted to account for changes in the user's insulin needs.

After the modified amount of the co-formulated drug for the next cycle for the new reservoir is calculated ($D_{co}(j)$), it may be output to the user with instructions or a recommendation for how much to insert into the next reservoir. Alternately, this modified amount can inform an automated drug co-formulation device that can automate the dosage of the appropriate amount of co-formulated GLP-1 or other drug when filling each new insulin reservoir. For example, the system may output to the user via a user interface 158 of user device 105 to insert or co-formulate 6.0 mg of GLP-1 per 200U of insulin, instead of the previous 3.0 mg of GLP-1 per 200U of insulin, which corresponds to a 100% increase in the concentration of GLP-1 within the 200U reservoir. This recommendation would be provided if the user's current total daily insulin need has been reduced to 50% of the original total daily insulin in which the original daily GLP-1 dose was prescribed by the physician, meaning each subsequent insulin dose must deliver double the amount of GLP-1 that was first delivered within the same insulin dose, to provide the same total amount of GLP-1 to the user per day. In this manner, concentrations of the secondary drug (e.g., GLP-1 or pramlintide) may be adjusted as the user's insulin needs change.

The following examples pertain to various embodiments of the systems and methods disclosed herein for implementation of an automatic drug delivery system dispensing a co-formulation of GLP-1 and insulin.

Example 1 is a method implementing a first embodiment of the invention comprising calculating a dose of insulin, calculating a reduction factor, calculating an adjusted dose of insulin by applying the adjustment factor to the calculated dose and delivering the adjusted dose to the user.

Example 2 is an extension of Example 1, or any other example disclosed herein, further comprising receiving a periodic blood glucose readings of the user, wherein the calculation of the dose of insulin and the reduction factor is triggered by the receipt of each new blood glucose reading.

Example 3 is an extension of Example 1, or any other example disclosed herein, wherein the calculated dose comprises a co-formulation of GLP-1 and insulin.

Example 4 is an extension of Example 3, or any other example disclosed herein, wherein the reduction factor reduces the size of the calculated dose delivered to the user to compensate for the effect of a quantity of GLP-1 in the co-formulation.

Example 5 is an extension of Example 1, or any other example disclosed herein, wherein the reduction factor is based on the concentration of GLP-1 within the co-formulation.

Example 6 is an extension of Example 5, or any other example disclosed herein, wherein the reduction factor is further based on the quantity of GLP-1 delivered to the user within a most recent predetermined period of time Example 7 is an extension of Example 6, or any other example disclosed herein, wherein the reduction factor is further based on a known reduction in the daily insulin need of the user affected by the concentration of GLP-1 delivered to the user in the co-formulation.

Example 8 is an extension of Example 7, or any other example disclosed herein, wherein an average reduction in the daily insulin need over population of users is used to calculate the reduction factor.

Example 9 is a system comprising a drug delivery device configured to deliver a co-formulation of insulin and an algorithm to determine the timing and quantity of the delivery of the co-formulation.

Example 10 is an extension of Example 9, or any other example disclosed herein, wherein the algorithm calculates a dose of insulin, calculates a reduction factor and applies the adjustment factor to the calculated dose to obtain an adjusted dose.

Example 11 is an extension of Example 10, or any other example disclosed herein, wherein the reduction factor is based on the concentration of GLP-1 within the co-formulation.

Example 12 is an extension of Example 11, or any other example disclosed herein, wherein the reduction factor is based on the quantity of GLP-1 delivered to the user within a most recent predetermined period of time.

Example 13 is an extension of example 12, or any other example disclosed herein, wherein the reduction factor is further based on a known reduction in the daily insulin need of the user effected by the concentration of GLP-1 delivered to the user in the co-formulation.

Example 14 is a method implementing a second embodiment of the invention comprising calculating a quantity of GLP-1 that has been delivered to user within a most recent predetermined period of time, calculating a correction factor, calculating a modified correction factor based on the correction factor and the calculated quantity of GLP-1, calculating a dose of insulin to be delivered to the user based on the modified correction factor and delivering the calculated dose of insulin to the user as part of a co-formulation of GLP-1 and insulin.

Example 15 is extension of Example 14, or any other example disclosed herein, further comprising calculating an insulin-to-carbohydrate ratio, calculating a modified insulin-to-carbohydrate ratio based on the calculated quantity of GLP-1 and calculating the dose of insulin to be delivered to the user based on the modified insulin-to-carbohydrate ratio.

Example 16 is an extension of Example 15, or any other example disclosed herein, wherein calculating the modified correction factor and insulin-to-carbohydrate ratio assumes an average effect of the delivery of the GOP-one and the co-formulation on the insulin sensitivity of a population of users.

Example 17 is an extension of Example 14, or any other example disclosed herein, wherein calculating a modified correction factor and I:C ratio assumes an average effect of the delivery of the GLP-1 in the co-formulation on the insulin sensitivity of a population of users.

Example 18 is a system implementing the second embodiment the invention comprising a drug delivery device configured to deliver a co-formulation of GLP-1 and insulin and an algorithm to determine the timing and quantity of the delivery of the co-formulation, wherein the algorithm calculates a quantity of GLP-1 that has been delivered to the user within a most recent predetermined period of time, calculates a correction factor, calculates a modified correction factor based on the correction factor and the quantity of GLP-1 and calculates a dose of insulin to be delivered to the user based on the modified correction factor.

Example 19 is an extension of Example 18, or any other example disclosed herein, wherein the algorithm further calculates an insulin-to-carbohydrate ratio, calculates a modified insulin-to-carbohydrate ratio based on the calculated quantity of GLP-1 and calculates the dose of insulin based on the modified insulin-to-carbohydrate ratio.

Example 20 is an extension of Example 19, or any other example disclosed herein, wherein, when bolus doses are being delivered to the user, the algorithm further calculates the quantity of GLP-1 that has been delivered to the user, accounting for expected changes in insulin sensitivity of the user due to additional GLP-1 that is delivered.

To those skilled in the art to which the invention relates, many modifications and adaptations of the invention may be realized. Implementations provided herein, including sizes, shapes, ratings and specifications of various components or arrangements of components, and descriptions of specific manufacturing processes, should be considered exemplary only and are not meant to limit the invention in any way. As one of skill in the art would realize, many variations on implementations discussed herein which fall within the scope of the invention are possible. Moreover, it is to be understood that the features of the various embodiments described herein were not mutually exclusive and can exist in various combinations and permutations, even if such combinations or permutations were not made express herein, without departing from the spirit and scope of the invention. Accordingly, the method and apparatus disclosed herein are not to be taken as limitations on the invention but as an illustration thereof. The scope of the invention is defined by the claims which follow.

The invention claimed is:

1. A method comprising:
calculating a quantity of a first drug that has been delivered to a user within a most recent predetermined period of time, wherein the first drug is GLP-1;
calculating a correction factor used in the calculation of a dose of insulin to be delivered to the user;
calculating a modified correction factor based on the calculated correction factor and the calculated quantity of the first drug that has been delivered to the user;
calculating a dose of insulin to be delivered to the user based on the modified correction factor, wherein calculating the dose of insulin comprises:
determining an insulin to carbohydrate (I:C) ratio used in the calculation of the dose of insulin to be delivered to the user,
calculating a modified I:C ratio based on the calculated quantity of GLP-1 that has been delivered to the user, and
calculating the dose of insulin to be delivered to the user based on the modified I:C ratio; and
delivering the calculated dose of insulin to the user;
wherein the calculated dose of insulin delivered to the user is delivered as a co-formulation of the first drug and insulin.

2. The method of claim 1 wherein, when the bolus doses are being delivered to the user, the method further calculates the quantity of GLP-1 that has been delivered to a user, accounting for expected changes in insulin sensitivity of the user due to additional GLP-1 that is delivered.

3. The method of claim 1 wherein calculating a modified correction factor and I:C ratio assumes an average effect of the delivery of the GLP-1 in the co-formulation on the insulin sensitivity of a population of users.

4. A system comprising:
a drug delivery device configured to deliver a co-formulation of insulin and a second drug to a user; and
an algorithm, implemented by software executed by a processor, to determine the timing and quantity of the delivery of the co-formulation of insulin and the second drug to the user, wherein the algorithm:
calculates a quantity of the second drug that has been delivered to a user within a most recent predetermined period of time, wherein the first drug is GLP-1;
calculates a correction factor used in the calculation of a dose of insulin to be delivered to the user;
calculates a modified correction factor based on the calculated correction factor and the calculate quantity of the second drug that has been delivered to the user; and
calculates a dose of insulin to be delivered to the user based on the modified correction factor, wherein calculating the dose of insulin comprises:
determining an insulin to carbohydrate (I:C) ratio used in the calculation of the dose of insulin to be delivered to the user,
calculating a modified I:C ratio based on the calculated quantity of GLP-1 that has been delivered to the user, and
calculating the dose of insulin to be delivered to the user based on the modified I:C ratio; and
wherein the drug delivery device delivers the calculated dose of insulin to the user.

5. The system of claim 4 wherein, when the bolus doses are being delivered to the user, the algorithm further calculates the quantity of the second drug that has been delivered to a user, accounting for expected changes in insulin sensitivity of the user due to additional amount of the second drug that is delivered.

* * * * *